US010472607B2

(12) United States Patent
Su et al.

(10) Patent No.: US 10,472,607 B2
(45) Date of Patent: Nov. 12, 2019

(54) CULTURE MEDIUM AND METHOD FOR INDUCING DIFFERENTIATION OF PLURIPOTENT STEM CELLS INTO NEUROEPITHELIAL CELLS

(71) Applicant: National Chung Hsing University, Taichung (TW)

(72) Inventors: Hong-Lin Su, Taichung (TW); Sheng-Mei Chen, Nantou County (TW)

(73) Assignee: NATIONAL CHUNG HSING UNIVERSITY, Taichung (TW)

( * ) Notice: Subject to any disclaimer, the term of this patent is extended or adjusted under 35 U.S.C. 154(b) by 0 days.

(21) Appl. No.: 14/932,507

(22) Filed: Nov. 4, 2015

(65) Prior Publication Data
US 2016/0108362 A1  Apr. 21, 2016

Related U.S. Application Data

(63) Continuation-in-part of application No. 13/485,914, filed on May 31, 2012, now abandoned.

(30) Foreign Application Priority Data

Dec. 14, 2011 (TW) ................................. 100146179

(51) Int. Cl.
 *A61K 35/30* (2015.01)
 *A61K 35/545* (2015.01)
 *C12N 5/0793* (2010.01)

(52) U.S. Cl.
 CPC ...... *C12N 5/0619* (2013.01); *C12N 2501/115* (2013.01); *C12N 2501/415* (2013.01); *C12N 2501/60* (2013.01)

(58) Field of Classification Search
None
See application file for complete search history.

(56) References Cited

U.S. PATENT DOCUMENTS

| | | | | |
|---|---|---|---|---|
| 2010/0166713 | A1* | 7/2010 | Dalton | C12N 5/0603 424/93.7 |
| 2013/0280804 | A1* | 10/2013 | Dalton | C12N 5/0623 435/368 |

OTHER PUBLICATIONS

Li et al., Rapid induction and long-term self-renewal of primitive neural precursors from human embryonic stem cells by small molecule inhibitors. PNAS | May 17, 2011 | vol. 108 | No. 20 | 8299-8304 (Year: 2011).*

(Continued)

*Primary Examiner* — Aurora M Fontainhas
(74) *Attorney, Agent, or Firm* — Muncy, Geissler, Olds & Lowe, P.C.

(57) ABSTRACT

The present invention discloses a culture medium and method for inducing differentiation of pluripotent stem cells into neuroepithelial cells. The culture medium comprises at least two agents for neural induction, wherein the agents includes a Wnt signal agonist and a Smad2/3 inhibitor and the culture medium is a feeder free culture. The method is to culture pluripotent stem cells in the culture medium to differentiate into neuroepithelial cells. The neuroepithelial cells can further differentiate into mature neurons for practical applications, including regeneration medicine and drug discovery for neural disorders.

4 Claims, 21 Drawing Sheets
(21 of 21 Drawing Sheet(s) Filed in Color)

(56) References Cited

OTHER PUBLICATIONS

Vallier et al., Early Cell Fate Decisions of Human Embryonic Stem Cells and Mouse Epiblast Stem Cells Are Controlled by the Same Signalling Pathways. PLOS ONE Jun. 2009 | vol. 4 | Issue 6 | e6082 (Year: 2009).*

Maintenance of pluripotency in human and mouse embryonic stem cells through activation of Wnt signaling by a pharmacological GSK-3-specific inhibitor; Noboru Sato et al.; Nature Medicine, vol. 10, No. 1, Jan. 2004.

BDNF promotes the growth of human neurons through crosstalk with the Wnt/β-catenin signaling pathway via GSK-3β; Jin-wei Yang et al.; Neuropeptides 54 (2015) 35-46; Aug. 15, 2015.

Wnt signaling and a Smad pathway blockade direct the differentiation of human pluripotent stem cells to multipotent neural crest cells; Menendez et al.; PNAS, 19240-19245, vol. 108, No. 48, Nov. 29, 2011.

* cited by examiner

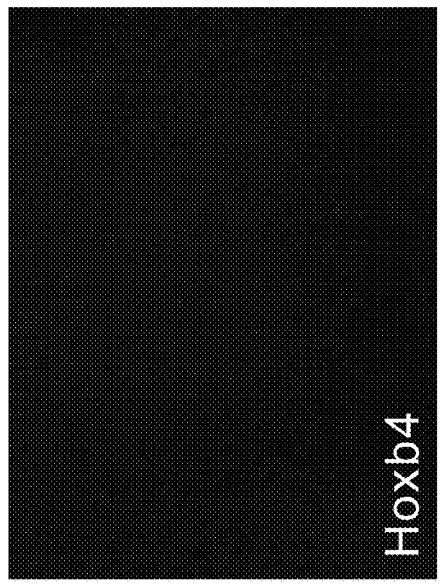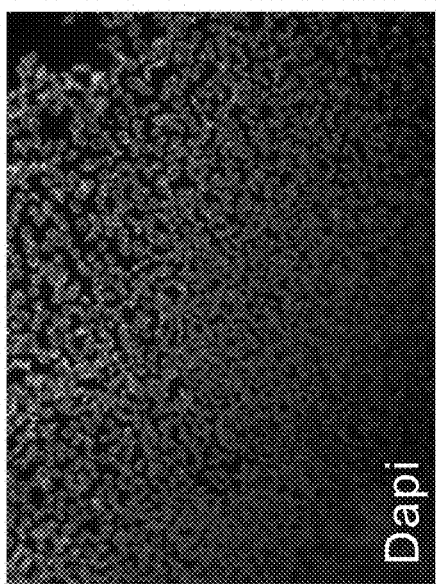
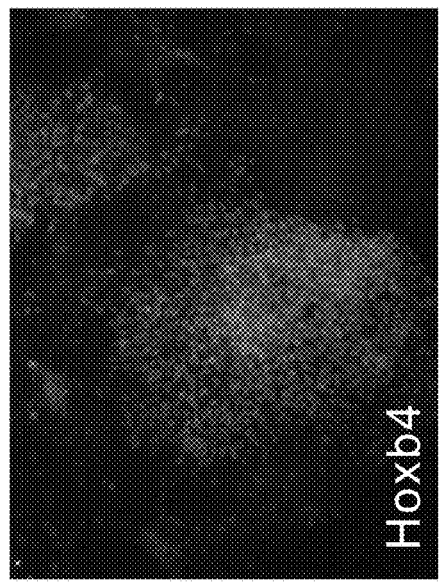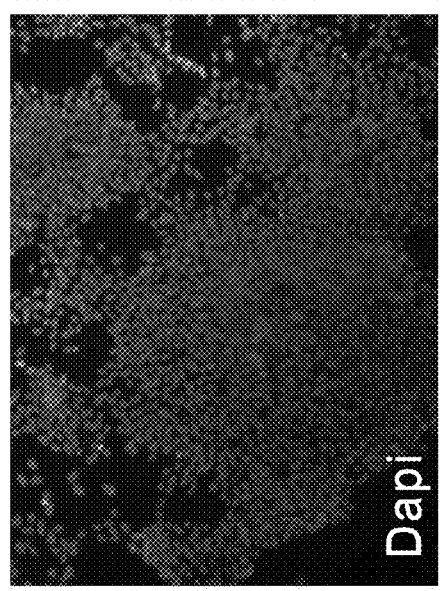
Fig. 15A  Fig. 15B ced neural cells renders non-neural cells
CULTURE MEDIUM AND METHOD FOR INDUCING DIFFERENTIATION OF PLURIPOTENT STEM CELLS INTO NEUROEPITHELIAL CELLS The current application is a continuation-in-part (CIP) of application Ser. No. 13/485,914 filed on May 31, 2012 which claims a foreign priority to application number 100146179 filed on Dec. 14, 2011 in Taiwan.

FIELD OF THE INVENTION

The present invention relates to the field of stem cell biology, in particular the linage specific differentiation of pluripotent or multipotent stem cells, which include, but not limited to, human embryonic stem cells (hESCs), human induced pluripotent stem cells (hiPSCs), human germinal stem cells, somatic stem cells, cancer stem cells, or any other cells capable of differentiation into three germ layers. Specifically, the present invention discloses the culture medium and method for inducing differentiation of pluripotent stem cells into primitive neuroepithelial cells.

BACKGROUND OF THE INVENTION

Stem cells are undifferentiated cells which exhibit the capacities for self-renewal and differentiation into more than two kinds of mature somatic cells. They are classified into totipotent stem cells, pluripotent stem cells, multipotent stem cells and bipotent stem cells according to their differentiation capacity. Furthermore, they are also classified into embryonic stem cells (ESCs), hematopoetic stem cells, mesenchymal stem cells and induced pluripotent stem cells (iPSCs) upon their origins. Herein, hESCs, derived from the inner cell mass of the human blastocyst, have shown the pluripotency for differentiating into all somatic cells. In addition, iPSCs, reprogrammed from differentiated somatic cells by introducing Yamananka factors or certain pluripotent factors, show pluripotency in vitro and in vivo and share ESC-like characteristics.

Many investigators have focused on the control of the stem cells differentiation into specific cell lineages with high efficiency. They attempt to apply these stem cells or their derivative cells to injured tissues for recovery of normal physiological functions. For example, the hESC-derived retina pigment epithelial (RPE) cells have been enriched in vitro and used to rescue the eye sight of patients with Stargardt Macular dystrophy and age-related macular degeneration after the cell transplantation.

Neural stem cells and stem cells-derived neurons benefit biomedical investigations in studying neural development, neural physiology, and development of new therapy for treating neural trauma and neuro-degeneration diseases. Therefore, robustly producing neuroepithelial cells, the most primitive precursor cells of embryonic nerve system, is highly potential for the above applications.

Many investigators have tried to induce neural differentiation of ESCs by adding fibroblast growth factor-2 (FGF-2) at the earliest step of differentiation under suspension culture (Li, X. J. et al., 2005; Timothy et al., 2009; Xu et al., 2005; Vallier, L. et al., 2005). Although this FGF2-dependent neural induction method can trigger the differentiation of ESCs into the neuroepithelial cells and show the cellular expression profile as the cells in neural groove of embryo, it usually spends 10-14 days for this stage of neural induction. In addition, some pluripotent stem cells are refractory to this method and show low efficacy of neural production. The low purity of ESC-derived neural cells renders non-neural cells contamination within the cultured population and hinders further clinical applications.

Dual Smad inhibition method has shown the high efficacy of neuroepithelial cell induction from pluripotent stem cells. Inhibitors of Smad 1/5/8 and Smad2/3, such as Noggin and SB431542 respectively, were added into the induction medium for shortening the time frame of the neural induction (Elkabetz et al., 2008; Lee et al., 2007; Chambers et al., 2009). In addition, genetic manipulations or co-culture with other cell lines were also reported to induce the neural differentiation of pluripotent stem cells.

Although the aforementioned methods for generating the neuroepithelial cells from pluripotent stem cells are available, their disadvantages, such as poor efficacy of neural differentiation, expansive cost, risks resulted from virus-mediated genetic manipulations and non-neural cells contamination, still limit the further application of neuroepithelial cells in clinics. In addition, the contaminated non-neural cells or undifferentiated stem cells in the cultured pool may affect further neural differentiation. Moreover, remaining undifferentiated pluripotent stem cells may bring the risk of teratoma formation if the cells are not cleared before transplantation into recipients.

Therefore, efficient production of primitive neuroepithelial cells with high purity will benefit the further differentiation into mature neural cells and improve the clinical reliability and safety.

SUMMARY OF THE INVENTION

In one of its aspects, the present invention provides a culture medium and method for inducing differentiation of pluripotent stem cells into neuroepithelial cells. The culture method is a feeder-free culture and the culture medium contains at least two agents for neural induction, wherein the agents are a Wnt signal agonist and a Smad2/3 inhibitor.

In a particularly useful embodiment, the culture medium further includes a growth factor. Preferably, the growth factor is FGF-signal agonist, such as FGF2, and the concentration of FGF-signal agonist ranges from 1 ng/ml to 100 ng/ml.

In another embodiment, the Wnt signal agonist is a glycogen synthase kinase 3β (GSK-3β) inhibitor.

Preferably, the Wnt signal agonist is BIO and the Smad2/3 inhibitor is SB431542. In the culture medium, the concentration of BIO ranges from 0.05 µM to 50 µM and the concentration of SB431542 ranges from 1 µM to 100 µM.

In one embodiment, a BMP signal inhibitor is absent from the culture medium. Preferably, the BMP signal inhibitor is noggin or dorsomorphin (also called compound C).

In a particularly useful embodiment, the culture medium comprises a basal medium, wherein the basal medium can be DMEM, MEM, DMEM/F12, neurobasal medium, MSC medium, NSC medium, N2-neurobasal medium, or modified N2-neurobasal medium. Furthermore, the present invention provides an additive to a culture medium for inducing differentiation of pluripotent stem cells into neuroepithelial cells. The additive includes a Wnt signal agonist and a Smad2/3 inhibitor.

In a particularly useful embodiment, the additive further includes a growth factor. Preferably, the growth factor is FGF-signal agonist and the concentration of FGF-signal agonist ranges from 1 ng/ml to 100 ng/ml.

In the embodiments, the FGF-signal agonist can be FGF2, ligand for FGF, activators of extracellular signal-related kinase (ERK), c-jun N-terminal kinase (JNK) or phosphoinositol-3 kinase (PI3K). Preferably, the FGF-signal agonist is FGF2.

In another embodiment, the Wnt signal agonist is a glycogen synthase kinase 3β (GSK-3β) inhibitor.

Preferably, the Wnt signal agonist is BIO and the Smad2/3 inhibitor is SB431542.

In a particularly useful embodiment, the concentration of BIO ranges from 0.05 μM to 50 μM and the concentration of SB431542 ranges from 1 μM to 100 μM.

Still furthermore, the present invention provides a method for inducing differentiation of pluripotent stem cells into neuroepithelial cells. The method comprises steps of:

(a) culturing the pluripotent stem cells into embryoid bodies by suspension culture, wherein the pluripotent stem cells are hESCs or iPSCs.

(b) culturing the embryoid bodies in the culture medium according to the present invention described above to obtain the neuroepithelial cells.

In one embodiment, the neuroepithelial cells from the step (b) can be further cultured to differentiate into mature neural cells. Preferably, the mature neural cells can be motor neurons or dopaminergic neurons.

In one embodiment, the method further includes a step (c), wherein the step (c) is to substitute the culture medium of step b to another culture medium for culturing the neuroepithelial cells. The another culture medium includes a basal medium for culturing neuroepithelial cells, and an agent for maintaining the neuroepithelial cells, such as FGF2. Preferably, the basal medium is DMEM, MEM, DMEM/F12, neurobasal medium, MSC medium, NSC medium, N2-neurobasal medium, or modified N2-neurobasal medium.

In a particularly useful embodiment, the basal medium is a feeder-free culture and absenting BMPs and/or GSK-3β inhibitors.

The culture and the additives, disclosed in the present invention, enable pluripotent stem cells to be effectively directed into neuroepithelial cells under the condition of neither feeder (e.g. stromal feeders) cells nor BMP signaling inhibitors (e.g. compound C described in US 2011/0305672). In addition, the present invention can efficiently shorten the time cost for acquiring the neuroepithelial cells from pluripotent stem cells with high purity.

The neuroepithelial cells indeed exhibit the expression of neural markers and forebrain markers including Nestin, Sox1, Pax6, Zic-1, N-cadherin (neural markers) and BF-1 (a forebrain marker). As a result, at least 90% of the resulting cells express the neural markers and forebrain markers.

Moreover, the neuroepithelial cells are capable of differentiation into all neural cells, such as cortical neurons of forebrain, dopaminergic neurons of midbrain and motor neurons of spinal cord. That is, the neuroepithelial cells can differentiate into mature neurons under the conditions of using the differentiating method known by person of ordinary skill in the art. For example, the neuroepithelial cells can differentiate into motor neurons by using a basal medium added with retinoic acid (RA) and sonic hedgehog (Shh) proteins.

More importantly, the neuroepithelial cells, obtained by using the method and the culture medium of the present invention, can highly differentiate into the spinal cord motor neurons. According to the invention, over 70% of the neuroepithelial cells differentiates into the motor neurons after the treating with RA and Shh. In contrast, the neuroepithelial cells, obtained by using the culture medium with noggin and SB431542 of the prior art, generally differentiate into motor neurons of spinal cord at an efficiency less than 20%.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 15A and 15B show the expression patterns of Hoxb4 in the cultured cells with treating retinoic acid at the culture day 10 by immunofluorescence staining.

DETAILED DESCRIPTION OF THE INVENTION

The present invention provides a culture medium and method for inducing differentiation of pluripotent stem cells into neuroepithelial cells. According to the present invention, it can induce neural differentiation of pluripotent stem cells into neuroepithelial cells and mature neural cells. As a result, more than 90% of the pluripotent stem cells can successfully differentiate into neuroepithelial cells.

The neuroepithelial cells highly express specific markers of embryonic neural tube, including Nestin, Sox1, Pax6, Zic-1 and N-cadherin, and forebrain markers, such as BF-1. In addition, the neuroepithelial cells can further differentiate into mature neural cells.

Figure 1A:
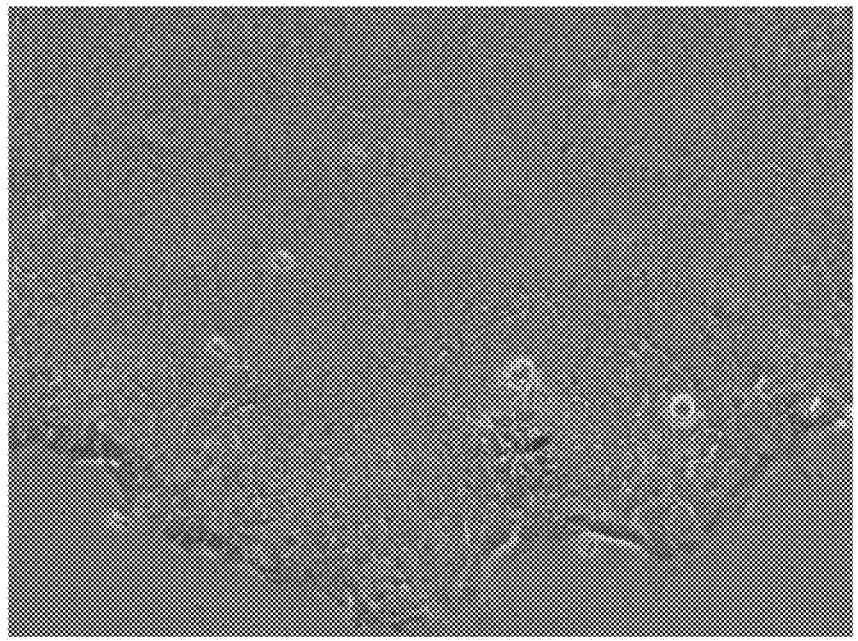
FIGS. 1A, 1B and 1C show the morphology and growth curve of the human embryonic stem cells which were cultured in mTESR1 medium without feeder cells.
Figure 1B:
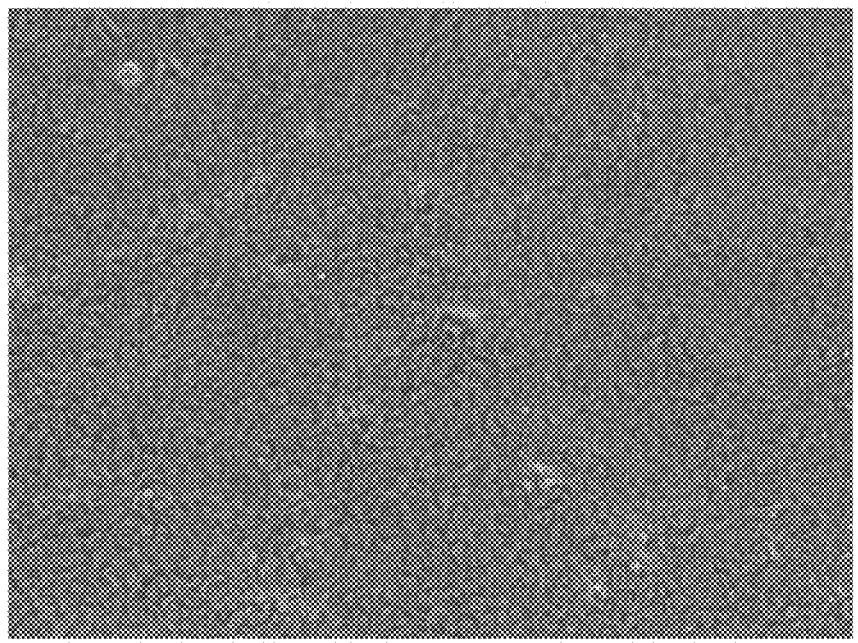
Figure 1C:
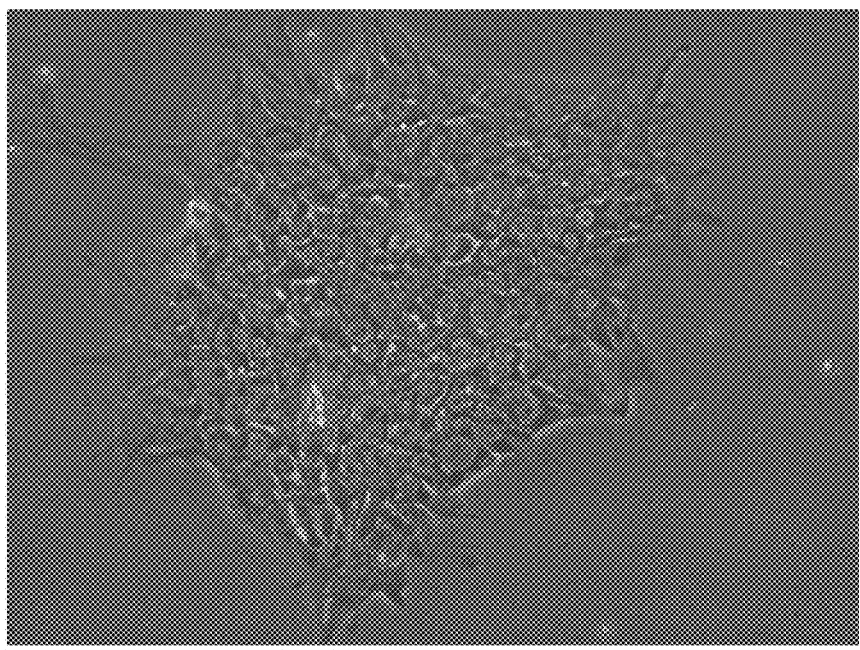

Definition of the terms as used herein as below:

The term "pluripotent stem cells" refers to include the mammalian ESCs, iPSCs and other pluripotent stem cells capable to differentiate into three germ layer cells. The pluripotent stem cells, TW1 cells, used in the following examples of the present invention is a hESC. FIGS. 1A to 1C reveal the growth curve of the TW1 cells cultured in mTESR1 medium without feeder cells.

The term "ESC markers" includes the transcription factors such as Oct4 and Nanog, which are only highly expressed in undifferentiated ESCs but not in differentiated ESCs. Therefore, the expressions of these ESC markers are applied to examine the pluripotent status of pluripotent stem cells.

The term "neuroepithelial cells" refers to the earliest neural stem cells of the mammalian nervous system, representing the epithelial cells of neural groove or neural tube of embryo. The neuroepithelial cells give rise to all neural cells in central nerve system and peripheral nerve system, such as radial glial cells, neural crest cells, mature neurons, astrocytes and oligodendrocytes. The characteristics of neuroepithelial cells are as the followings: (1) expressing specific markers of primitive neural tube and forebrain markers; (2) presenting as columnar appearance on a culture dish; (3) organizing with the neighbor cells by tightly tubular attachment around the edge to form the columnar structure; and (4) also called as neural rosettes.

The term "markers of neuroepithelial cells" refers to the genes such as Nestin, Sox1, Pax6, Zic-1 and N-cadherin, which are specifically expressed in the neuroepithelial cells. These neural markers are well-known indicators to verify whether the pluripotent stem cells have differentiated into neuroepithelial cells.

The term "forebrain markers" refers to the specific proteins restrictly expressed in the cells of embryonic forebrain, such as brain factor 1(BF1) and Forse1. The expression of this forebrain marker can be used to verify whether the pluripotent stem cells have differentiated into neuroepithelial cells.

The term "mature neuronal markers" refers to the specific proteins expressed in well-differentiated neurons, such as microtubule-associated protein 2 (MAP2) and βIII tubulin (recognized by Tuj1 antibody).

The term "markers of motor neurons" refers to the specific genes, such as HOXB4, olig2, and MNR2, which are restrictly expressed in the motor neurons of spinal cord.

The term "dopaminergic neuron" refers to a dopamine-producing neuron that expresses tyrosine hydroxylase (TH), neuron-specific enolase (NSE), and aromatic L-amino acid decarboxylase.

The term "BIO", 6-bromoindirubin 3'-oxime, refers to a specific inhibitor of glycogen synthase kinase-3β (GSK-3β). BIO exhibits the chemical formula as $C_{16}H_{10}BrN_3O_2$ and the structure as

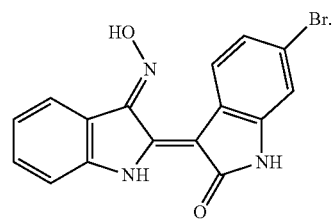 [SMILES: O=C1Nc2cc(Br)ccc2/C1=C1/Nc2ccccc2/C1=N\O]

The term "SB431542" is an potent and selective inhibitor of transforming growth factor β (TGFβ) superfamily I activin-like kinase (ALK) receptor, but not BMP-like receptor. It exhibits the chemical formula as $C_{22}H_{16}N_4O_3$ and molecular structure as

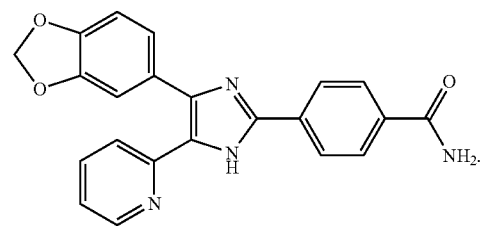 [SMILES: NC(=O)c1ccc(-c2nc(-c3ccc4c(c3)OCO4)c(-c3ccccn3)[nH]2)cc1]

The term "FGF-signal agonist" includes FGF2, ligand of FGF receptor, activators of ERK, JNK or PI3K. Herein, the FGF-signal agonist used in the following example of the present invention is FGF2.

The terms "basal medium" is used to describe a cellular growth medium in which necessary additives for cell growth or differentiation are not included.

The culture medium of this invention are well known in the art and include at least one basal medium plus one or more optional components. The basal medium is minimum essential medium (MEM) such as Eagle's culture medium, Dulbecco's modified Eagle's medium (DMEM), DMEM/F12, neurobasal medium, MSC medium, NSC medium, N2-neurobasal medium, and modified N2-neurobasal medium. These culture media are well-known in this field.

Furthermore, the optional components can be the agents for culturing the neuroepithelial cells. The terms "agents for culturing the neuroepithelial cells" refers to the additives for culturing neuroepithelial cells, such as N2 supplement, or heparin.

The terms "a" or "an" are defined as one or as more than one.

The following examples are provided to further illustrate the present invention. The claim of the invention is not limited to what are shown in the following experiments.

Example 1

Generation of Embryoid Bodies from ESCs

The TW1 cells, showing the classic morphology of hESCs (FIG. 1), were cultured and maintained in mTESR1 medium at 37° C. and 5% CO2. After the stage of cell expansion, the ESCs were dissociated with collagenase I and dispase for 5 mins at 37° C. The suspended cells were cultured in DMEM-F12 medium containing 20% knock-out serum replacement (KSR, Invitrogen, USA) at 37 and 5% CO2. These suspended ESCs gradually aggregated together and formed cell clusters, named as embryoid bodies, within 2 days culture.

Example 2

Induction of the Neural Differentiation of Pluripotent Stem Cells into Neuroepithelial Cells The embryoid bodies in example 1 were collected into a 15 ml centrifuge tube and placed for 10 mins until the embryoid bodies decended to the tube bottom. The supernatant was removed and replaced with neural induction medium, containing 0.5 µM BIO, 10 µM SB431542 and 10 ng/ml FGF2. The constitutions of the neural induction medium are listed in Table 1.

Notably, an announcement has to be emphasized here is that the working concentration of these additive drugs in the culture medium are not restricted on what we indicated. The working concentration of BIO is between 0.05 µM to 50 µM; the working concentration of SB431542 is between 1 µM to 100 µM; and the working concentration of FGF2 is between 1 ng/ml to 100 ng/ml.

Figure 2:
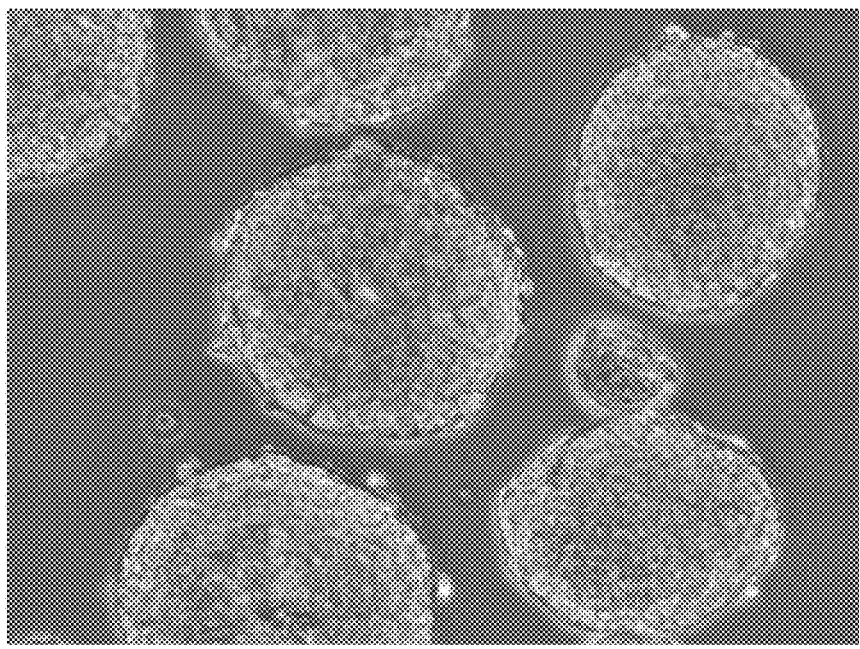
FIG. 2 shows the morphology of the cells which were cultured by suspension culture with the first neural induction medium.

The collected embryoid bodies were further cultured with the neural induction medium for 2 days to become neuroepithelial cells as shown in FIG. 2. In FIG. 2, the columnar neuroepithelial cells reveal the tightly tubular arrangement at the outer edge.

TABLE 1

The constitution of neural induction medium

| Constitutes | Content |
| --- | --- |
| DMEM medium (GIBCO, Lot no. 11965-092) | 326 ml |
| DMEM-F12 (GIBCO, Lot no. 11765-054) | 163 ml |
| N2 Supplement (GIBCO, Lot no. 17502-048) | 5 ml |
| MEM non-essential amino acid (Lot. M7145, Sigma) | 5 ml |
| Heparin (1 mg/ml) | 1 ml |

Example 3

Further Culturing the Neuroepithelial Cells

The culture medium of the neuroepithelial cells in example 2 was switched from the neural induction medium to next medium which comprise 10 ng/ml FGF2. The constitutions of the new medium are listed in Table 2 as below. The culture medium were renewed every two days to maintain the stemness of the neuroepithelial cells.

Figure 3A:
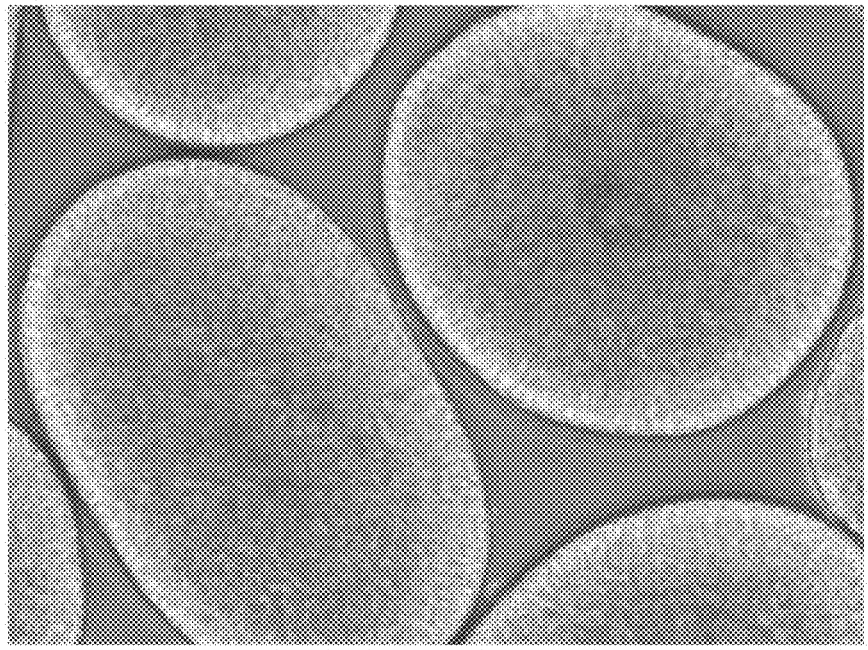
FIG. 3A shows the morphology of the cultured cells under microscope observation with 100× magnification.
Figure 3B:
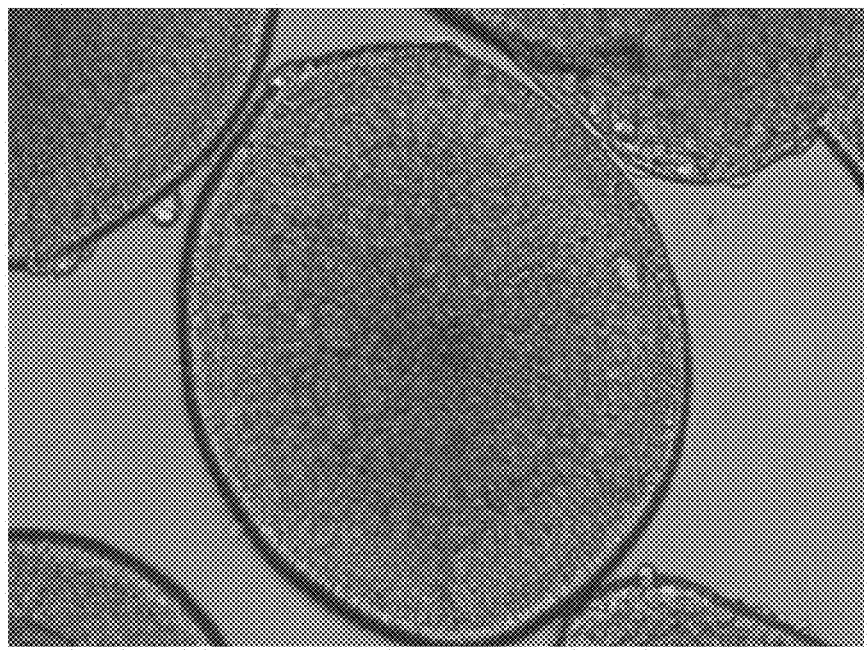
FIG. 3B shows the morphology of the cultured cells under microscope observation with 200× magnification.
Figure 3C:
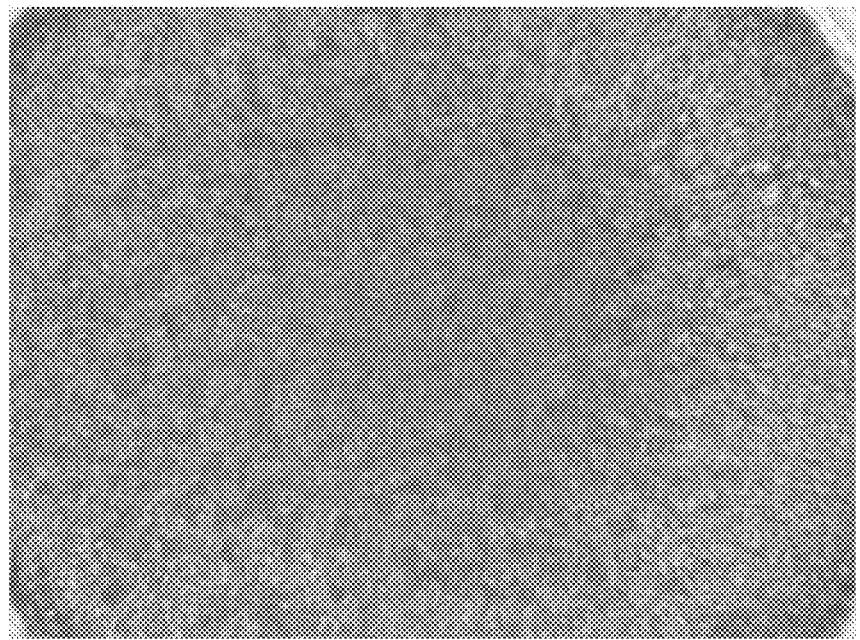
FIG. 3C shows the morphology of the cultured cells under microscope observation with 400× magnification.
Figure 4A:
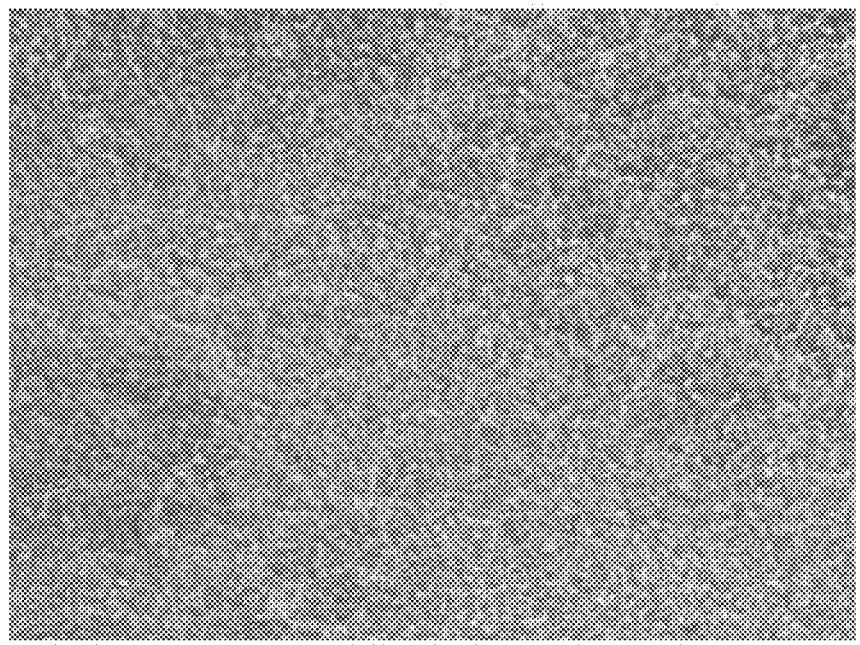
FIG. 4A shows the morphology of the differentiated neuroepithelial cells which adhered on a culture dish and aggregated to form the neural tube-like structure at culture day 6.
Figure 4B:
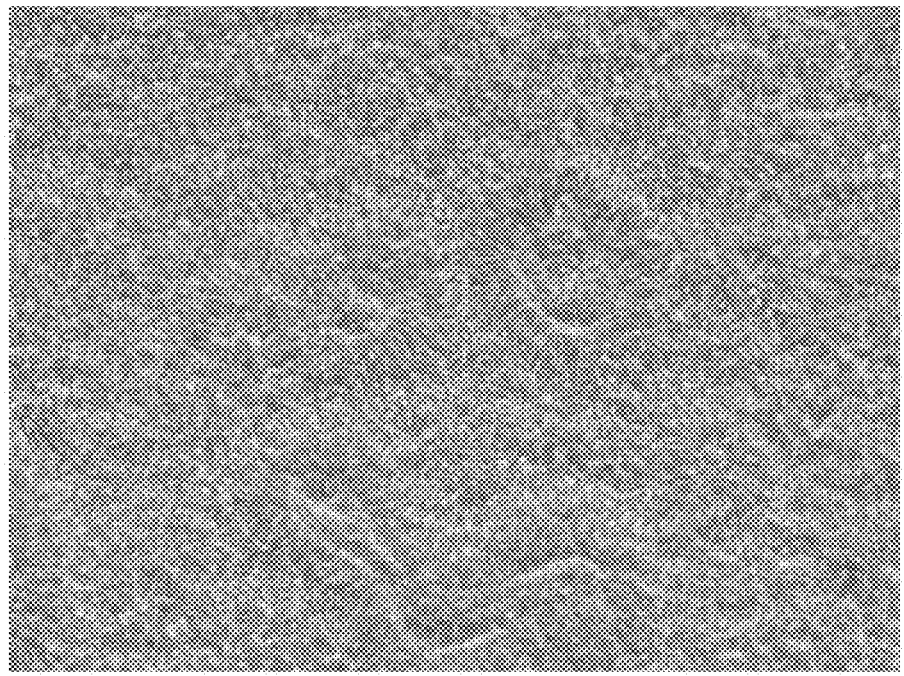
FIG. 4B shows the classical morphology of neural rosettes in the embryoid bodies at culture day 8.

The resulting cells were shown in FIG. 3 and FIG. 4 with 100×, 200×, and 400× magnifications under a microscope. In FIG. 3A, the resulting cells formed numerous columnar structure units among the embryoid bodies and shared with homogenous morphology. The FIGS. 3B and 3C revealed the columnar structure unit which contained the tightly tubular aggregation at the edge and rosette formations, resembling the early neural tube of embryo. The FIGS. 4A and 4B showed the classical morphology of neural rosettes within attached embryoid bodies on a culture dish at culture day 6 and day 8. Therefore, according to the examination of the morphology of the cells cultured from example 1 to example 3, it demonstrates that pluripotent stem cells can be rapidly and efficiently induced into the neuroepithelial cells by the neural induction medium and method of the present invention.

TABLE 2

The culture medium for neuroepithelial cells

| Constitutions | Content |
| --- | --- |
| Neurobasal medium (GIBCO) | 500 ml |
| N2- supplement (GIBCO) | 5 ml |
| Non-essential amino acid (NEAA, Sigma) | 5 ml |
| Heparin (1 mg/ml) | 1 ml |

Example 4

Preparation for the Immunofluorescence Staining

The embryoid bodies acquired in example 3 were seeded on 1% Matrigel-coated cover slides and cultured at 37, 5% CO2. The embryoid bodies adhered on the slides and exhibited neural rosettes morphology after one or two days culture.

Example 5

Preparation of Primary Antibodies and Secondary Antibodies

In order to identify the cell identity and efficacy of the neural conversion, we performed the immunofluorescent staining with appropriated primary antibodies and corresponding secondary antibodies. Therefore, the resulting cells of the example 3 were incubated with primary antibodies diluted in PBS, which contains 3% horse serum, at 4 for 24 hours. After the incubation with primary antibodies, the resulting cells were further incubated with corresponding fluorescence conjugated secondary antibodies with 1:500 dilution in dark at room temperature for one hour. Herein, the antibodies with suitable dilution ratio and the corresponding secondary antibodies were listed in Table 3.

TABLE 3

Antibodies used in the immunofluorescence staining

| Primary antibody | Species origin of primary antibody | Dilution | Secondary antibody |
| --- | --- | --- | --- |
| Oct4 | Goat | 1:200 | Cy3, FITC |
| Sox2 | Rabbit | 500 | Cy3, FITC |
| Nanog | Rabbit | 500 | Cy3, FITC |
| Nestin | Rabbit | 1:200 | Cy3, FITC |
| Pax6 | Rabbit | 1:200 | Cy3, FITC |
| Sox1 | Goat | 1:200 | Cy3, FITC |
| Zic-1 | Rabbit | 1:200 | Cy3, FITC |
| N-cadherin | Mouse | 1:200 | Cy3, FITC |
| ZO-1 | Rabbit | 1:100 | Cy3, FITC |
| BF-1 | Rabbit | 1:100 | Cy3, FITC |
| βIII tubulin | Mouse | 1:500 | Cy3, FITC |

Example 6

Identification of Neuroepithelial Cells by Immunofluorescent Staining

The cells on the cover slides were fixed with 4% paraformaldehyde at 4 for 5 minutes and followed by triplicated PBS washing. Cell membranes of fixed cells were permeabilized by 0.3% Triton in PBS at 4 for 5 minutes, and followed by PBS washing for 5 minutes twice. Non-specific and common antigens were masked by a blocking buffer containing 5% horse serum in PBS at room temperature for one hour. After the removal of the blocking buffer, the primary antibodies prepared in example 5 were added for staining the cells at 4 for overnight. After primary antibodies staining and triplicated PBS washing, the corresponding fluorescence-conjugated secondary antibodies were added for labelling the primary antibodies and incubated for 30 mins at room temperature in dark. Cell nuclei were stained by 1 μg/ml DAPI dye in PBS in dark at room temperature for 10 minutes. The fluorescent signals were observed under a fluorescent microscope and the ratios of labelled cell numbers were calculated by a software, AlphaEaseFC.

Figure 5A:
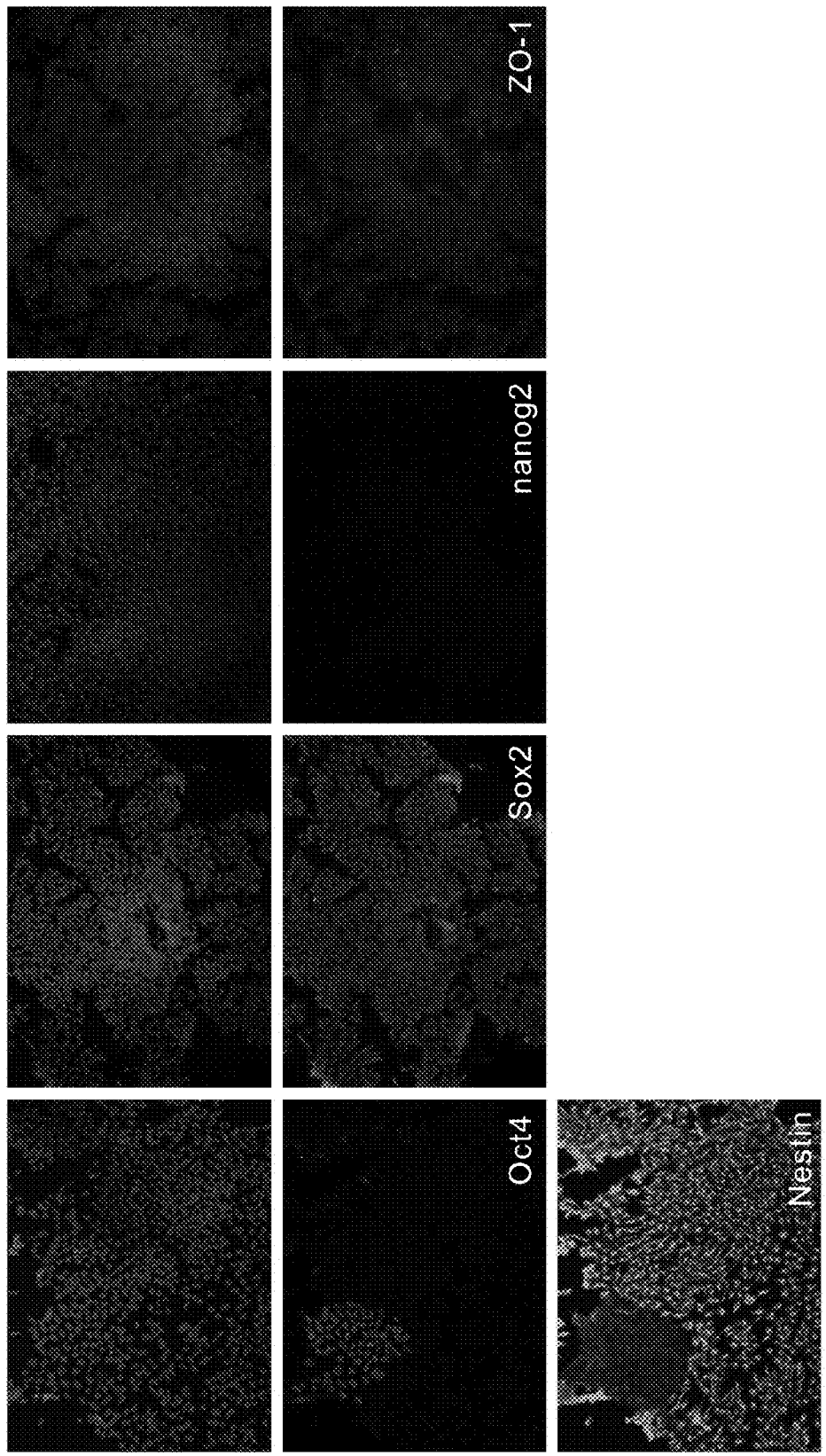
FIG. 5A shows the expression patterns of Oct4, Nestin, Sox2, Nanog and Zo-1 in the cultured neuroepithelial cells, examined by immunofluorescence staining with the corresponding primary antibodies.
Figure 5B:
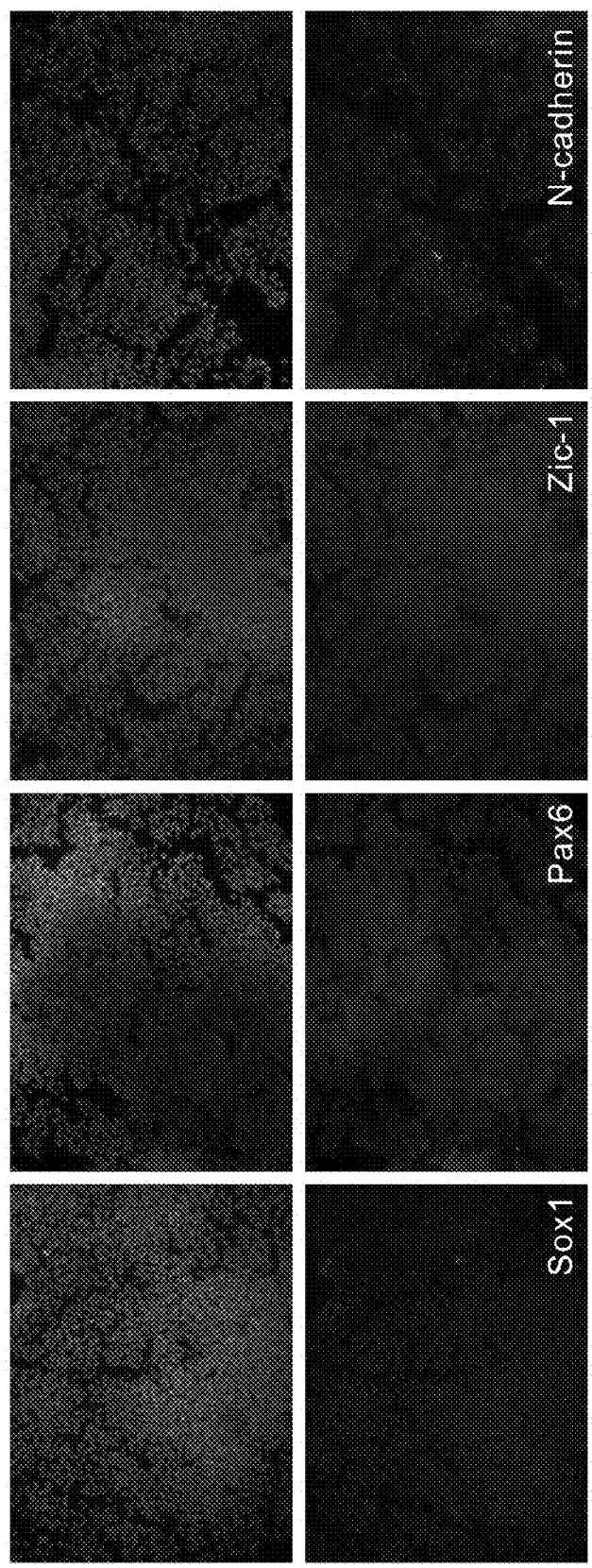
FIG. 5B shows the expression patterns of Sox1, Pax6, Zic1 and N-cadherin in the cultured neuroepithelial cells, examined by immunofluorescence staining with the corresponding primary antibodies.
Figure 5C:
FIG. 5C shows the expression patterns of BF1 in the cultured neuroepithelial cells, examined by immunofluorescence staining with the corresponding primary antibody.
Figure 5C:
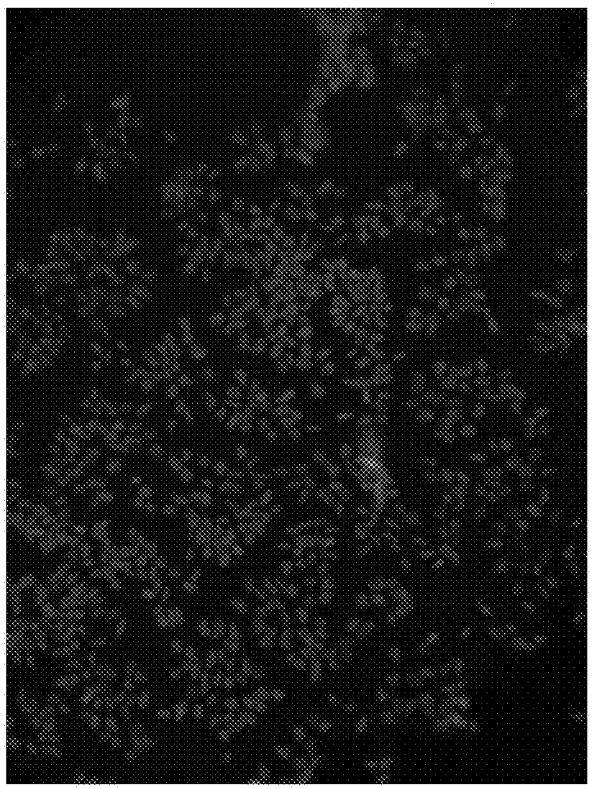
Figure 5D:
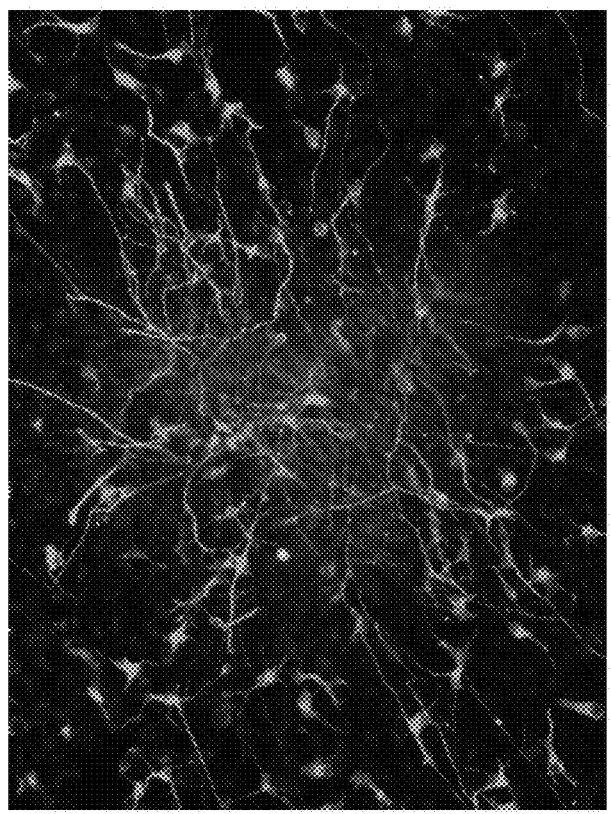
FIG. 5D shows the expression pattern of βIII tubulin in the adherent neuronal cells, examined by immunofluorescence staining with the corresponding primary antibody.

The protein expression observed by a fluorescent microscope was shown in FIG. 5, wherein the FIG. 5A revealed the protein expressions of Oct4, Nestin, Sox2, Nanog and ZO-1 at the induction day 10. The FIG. 5B showed the protein expressions of Sox1, Pax6, Zic1 and N-cadherin and FIG. 5C revealed the protein expressions of BF1, a forebrain marker, at the induction day 10. FIG. 5D revealed the protein expression of βIII tubulin, a mature neuron marker, in the ESC-derived cells at culture day 10. After the manual counting and software analysis for the immunolabelled cells, the results were summarized in Table 4, showing the high expressions of the neural markers and forebrain markers in the differentiating ESCs. In addition, the expressions of Nanog, a marker for undifferentiated pluripotent stem cells, were absent in the resulting cells after 10 days neural induction.

TABLE 4

The expression of stem cells, neural and forebrain markers

| Oct 4 | nanog | Sox2 | Nestin | Zo-1 | N-cadherin | Sox1 | Pax6 | Zic-1 | BF1 |
|---|---|---|---|---|---|---|---|---|---|
| 6.7% | 0% | 98% | 93.3% | 98% | 98% | 87.9% | 67% | 89% | 95.6% |

According to the Table 4 and FIGS. 5A to 5D, in the differentiating ESCs, the expression of pluripotent proteins was rapidly decreased but their expression of neural markers was dramatically increased. Furthermore, over 90% differentiating cells expressed a forebrain marker, BF1, at culture day 10. Therefore, the culture medium and method of this present invention is able to rapidly induce the differentiation of pluripotent stem cells into the neuroepithelial cells with high purity.

Example 7

The Neural Induction Medium of this Invention Triggers the Differentiation of Pluripotent Stem Cells into Neuroepithelial Cells The TW1 hESCs were divided into four groups according to the additives at culture day 3. The additives used in the four groups were listed in Table 5. The detail of the above steps refers to the examples 1 to 3.

TABLE 5 the additive drugs in the four groups.

| group | additive components |
|---|---|
| 1 | FGF2 |
| 2 | SB431542、FGF2 |
| 3 | BIO、SB431542 |
| 4 | SB431542、BIO、FGF2 |

Figure 6:
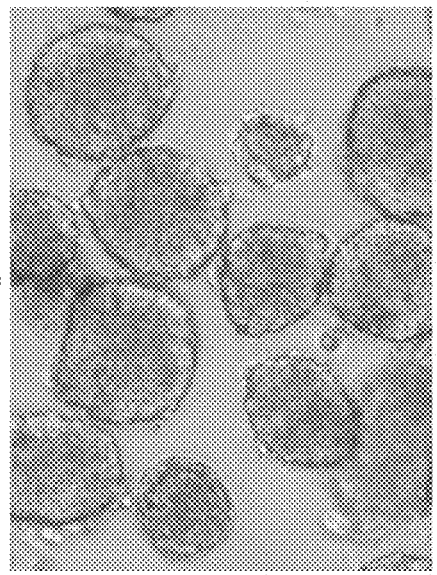
FIG. 6 shows the morphology of the cells of the each group at the culture day 5.
Figure 6:
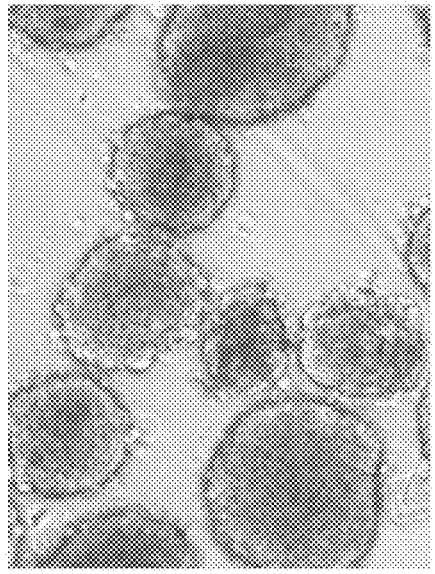
Figure 6:
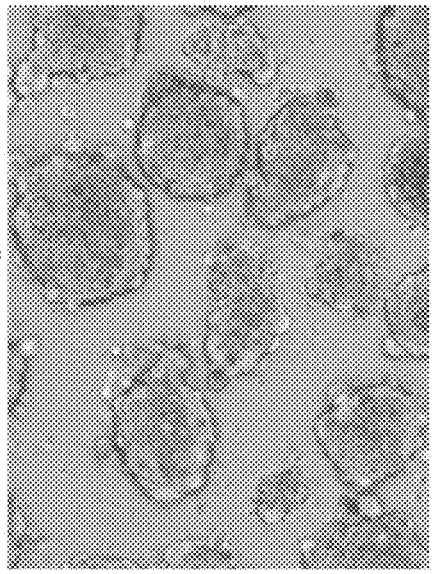
Figure 6:
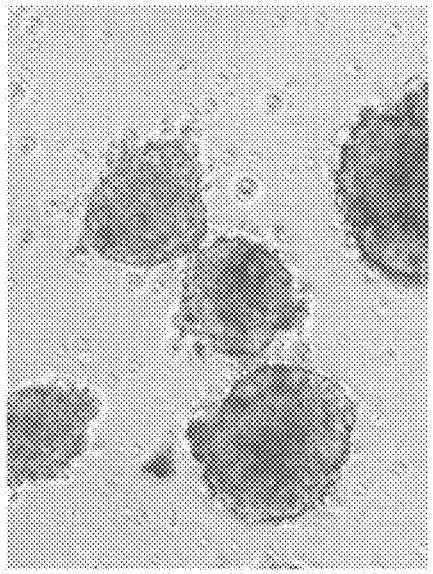
Figure 7:
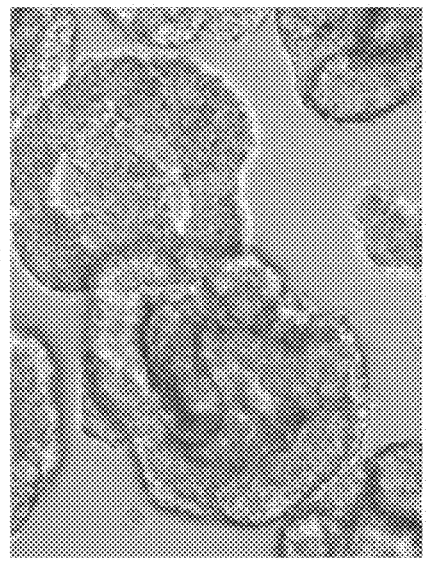
FIG. 7 shows the morphology of the cells of the each group at the culture day 7.
Figure 7:
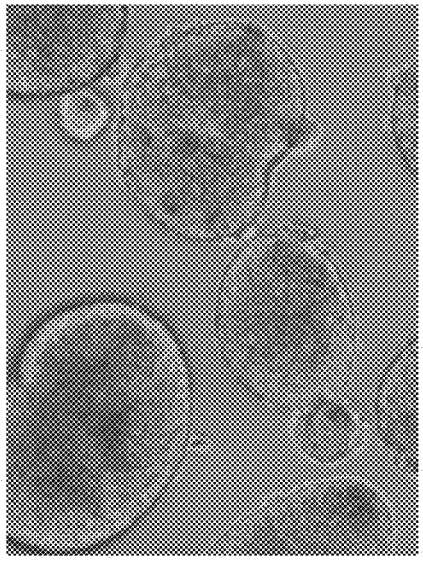
Figure 7:
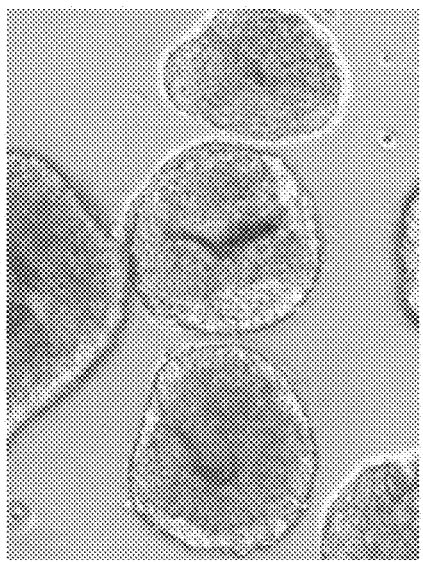
Figure 7:
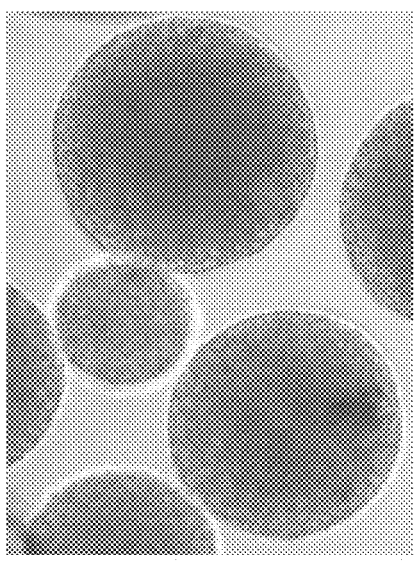
Figure 8:
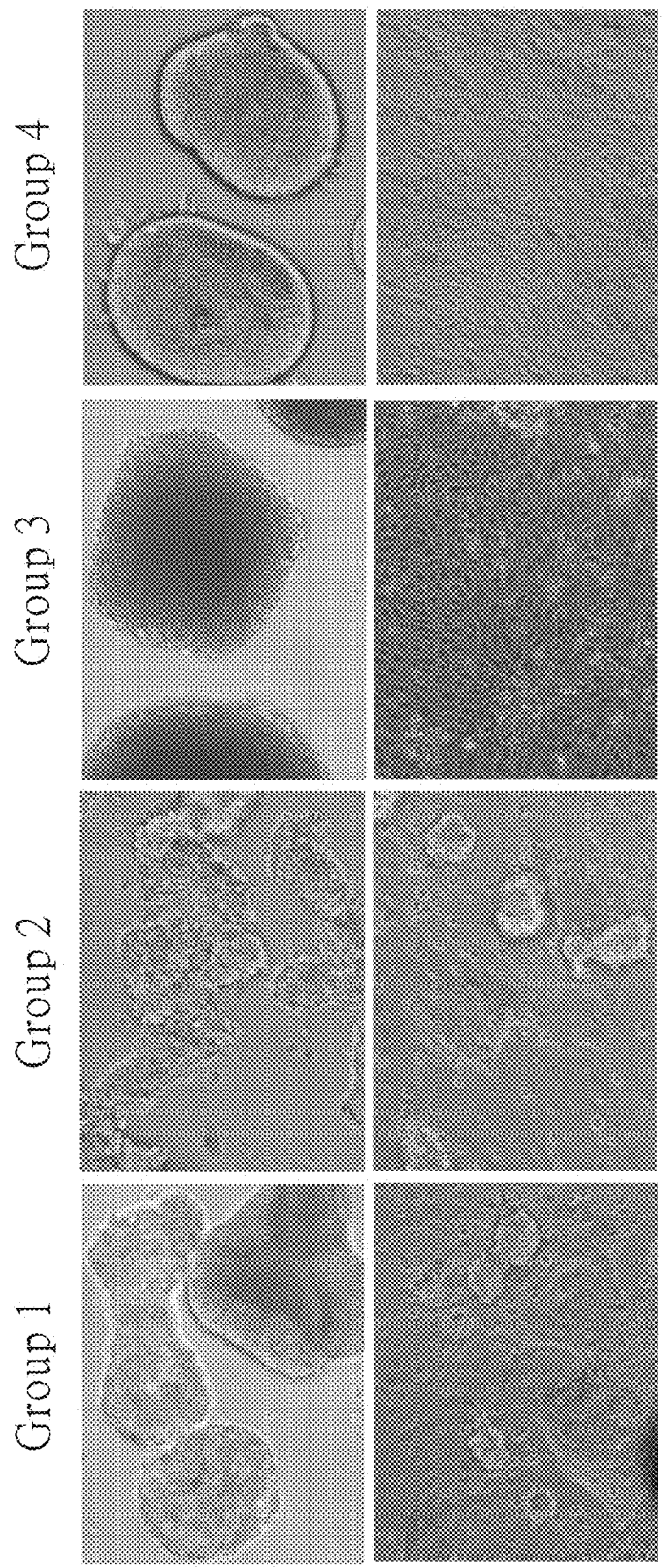
FIG. 8 shows the morphology of the cells of the each group at the culture day 10.
Figure 9:
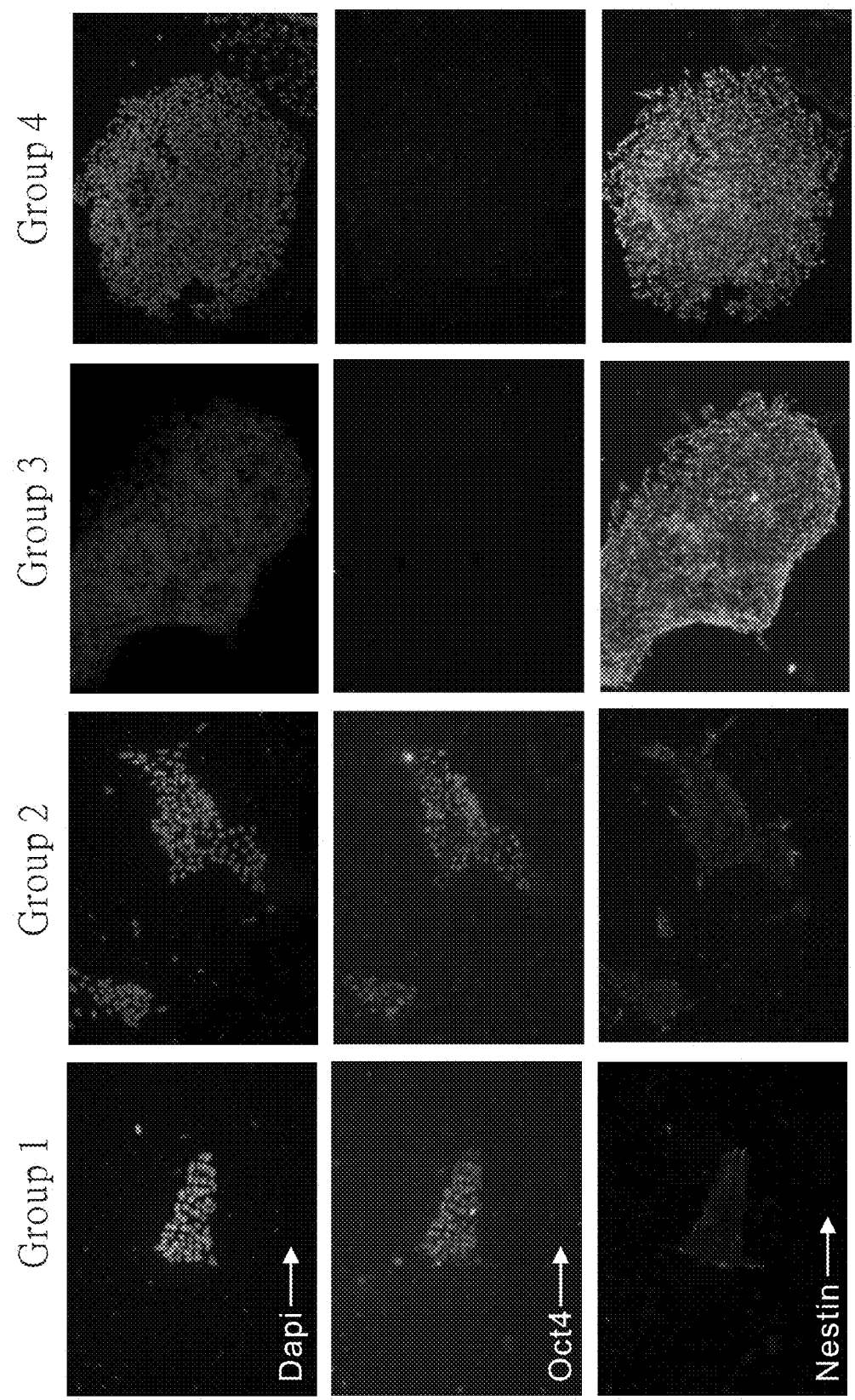
FIG. 9 shows the expression patterns of Oct4 and Nestin in the each group by immunofluorescence staining.

The cultured cells of the each group were observed at the culture day 5, 7 and 10 under a microscope and the results were shown in FIGS. 6 to 8. Referring to the methods in examples 5 and 6, the protein expressions of Oct4 and Nestin in the each groups and the results were examined and shown in FIG. 9.

According to the results of FIGS. 6 to 8, it showed that both the group 3 and the group 4, but not group 1 and group 2, formed the tight cell aggregation and sphereral morphology. Comparing to the group 3, adding FGF2 further enhanced the compaction and neural rosettes formation. In addition, Oct4, a well-characterized ESC marker, was detected in the groups 1 and 2, but not groups 3 and 4 at culture day 10. Moreover, a neural stem cell marker, Nestin, was robustly expressed in the groups 3 and 4. These results suggested that the neural induction medium, containing BIO/SB431542 or BIO/SB431542/FGF2, can robustly induce the differentiation of pluripotent stem cells into neuroepithelial cells.

Example 8

The Neuroepithelial Cells Show the Features of Forebrain Neurons

Referring to examples 1 to 3, the neuroepithelial cells, differentiated from the pluripotent stem cells, were further cultured in N2-neurobasal medium for 16 days (the culture day 5 to day 20). During the further culturing period, the expressions of the forebrain markers, such as BF1 and Forse1, were examined by the immunofluorescent staining and shown in FIGS. 10 and 11, respectively.

Figure 10:
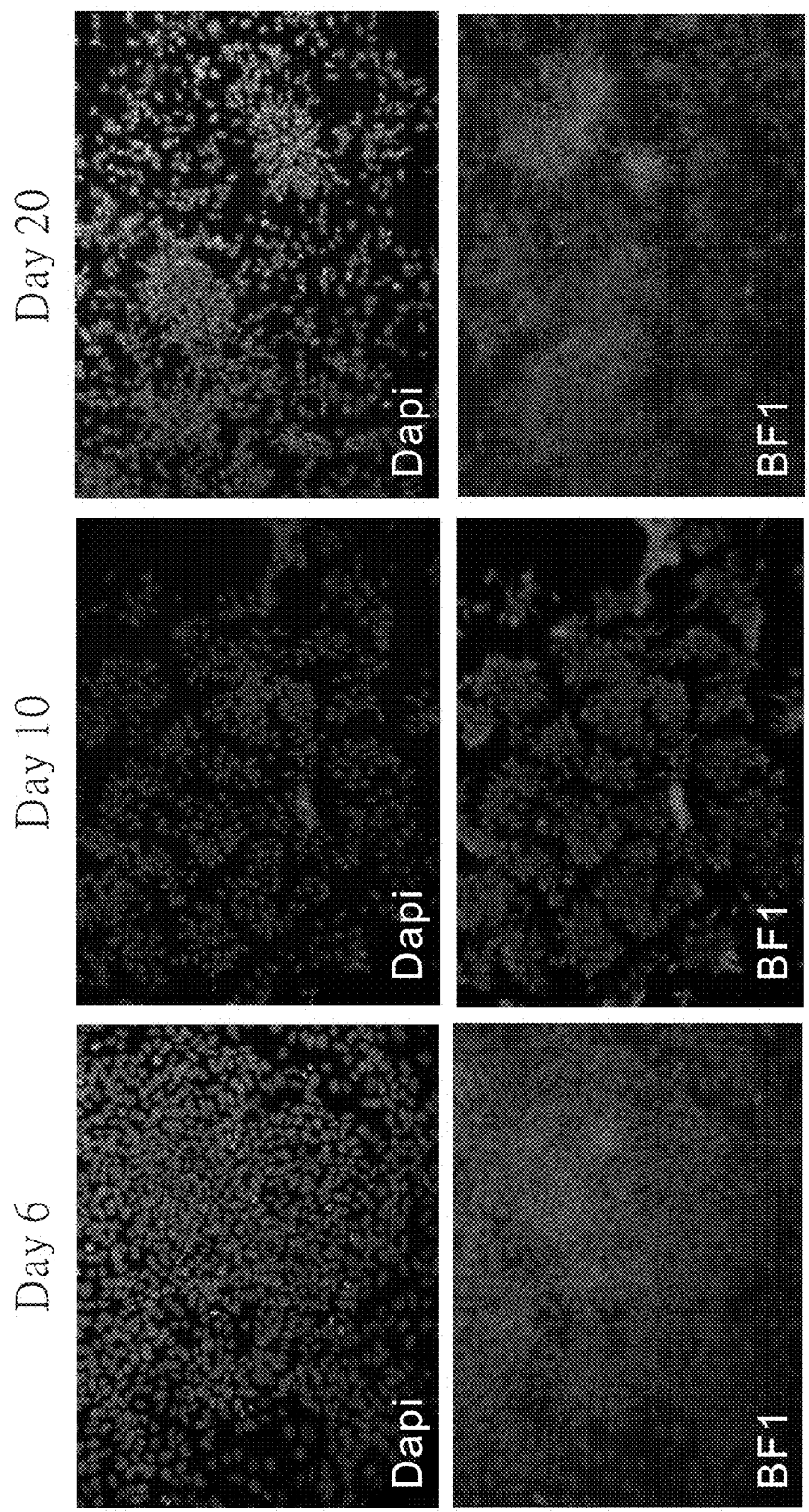
FIG. 10 shows the expression patterns of BF1 in the cultured cells at the culture day 6, 10 and 20 by immunofluorescence staining.
Figure 11:
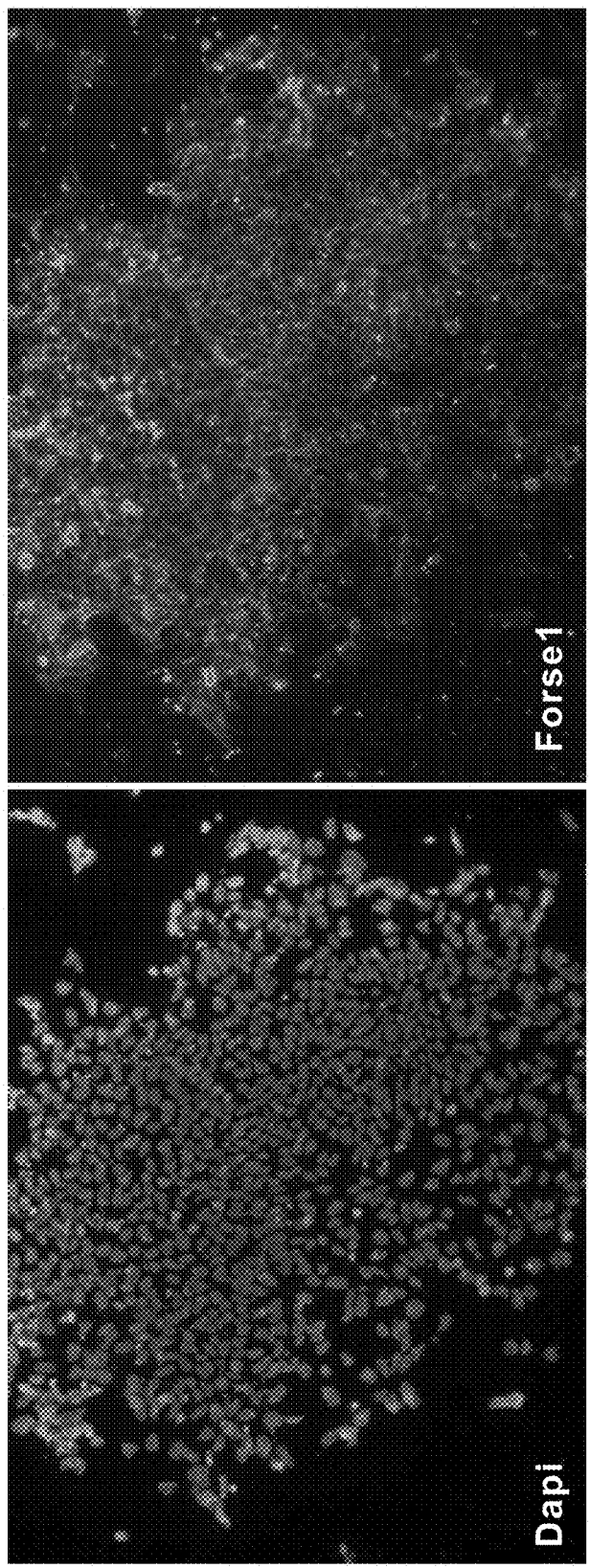
FIG. 11 shows the expression patterns of Forse1 in the cultured cells at the culture day 10 by immunofluorescence staining.

In both FIGS. 10 and 11, over 90% differentiating cells expressed the forebrain markers, demonstrating that the neuroepithelial cells possess the features of forebrain cell fate.

Example 9

Figure 12:
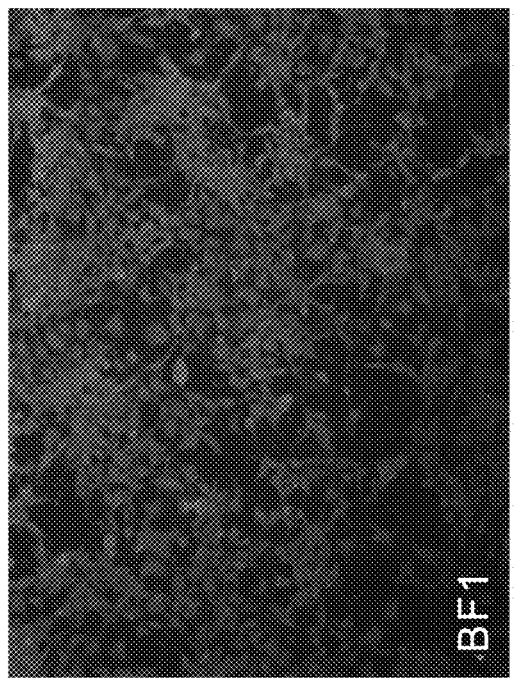
FIG. 12 shows the expression patterns of BF1 and βIII tubulin in the cultured cells by immunofluorescence staining.
Figure 12:
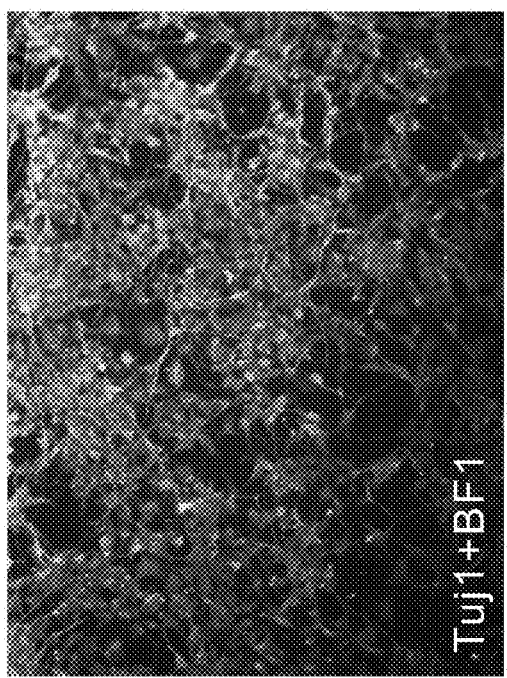
Figure 12:
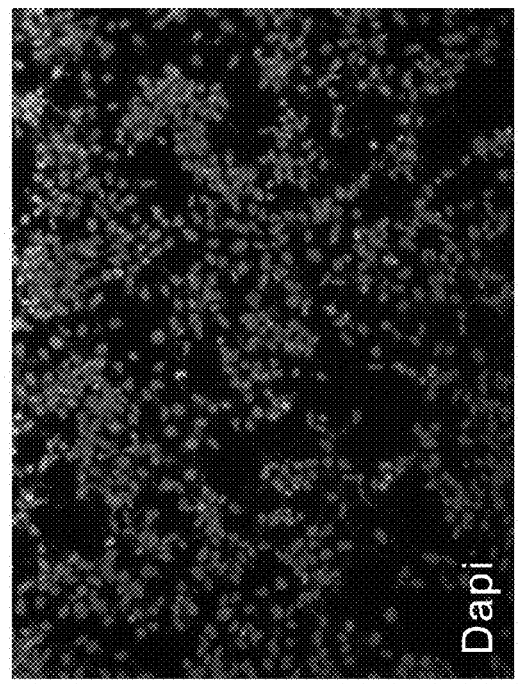
Figure 12:
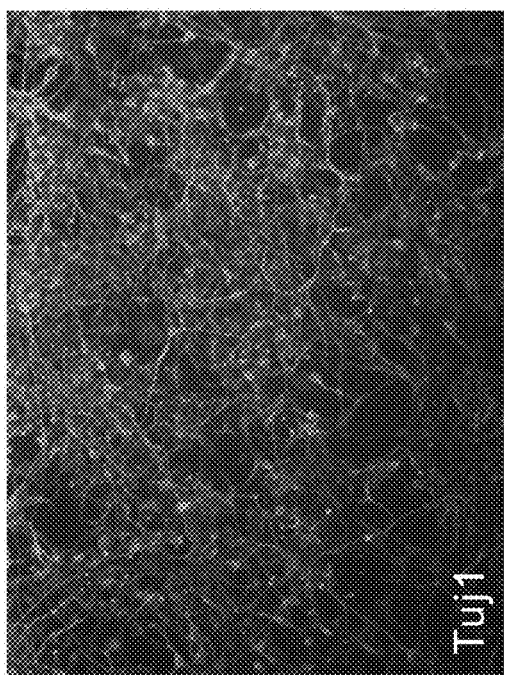
Figure 13:
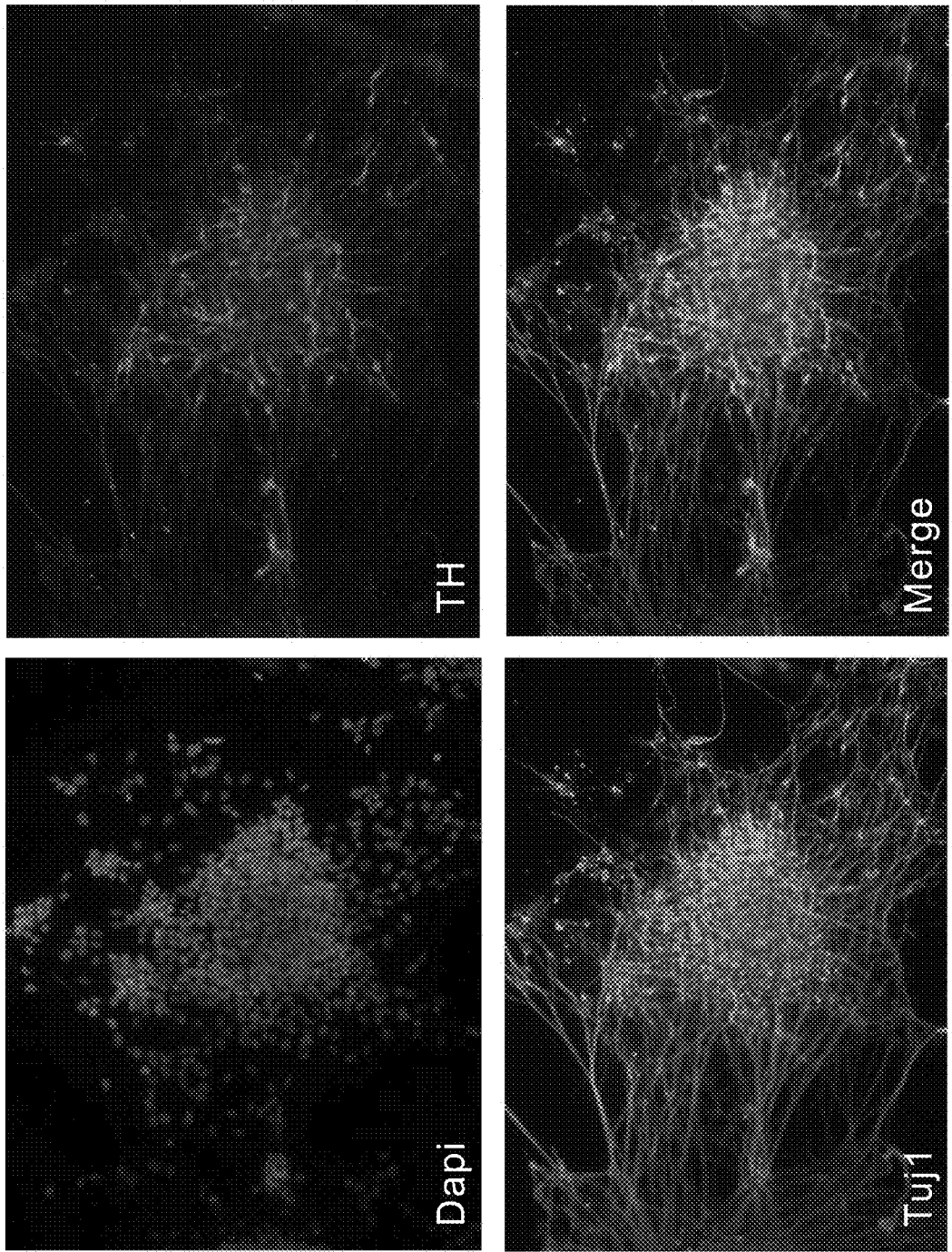
FIG. 13 shows the expression patterns of TH and βIII tubulin in the cultured cells by immunofluorescence staining.

The Neuroepithelial Cells can Further Differentiate into Mature Neurons, Such as Forebrain Cortical Neurons, Midbrain Dopaminergic Neurons and Spinal Cord Motor Neurons The neuroepithelial cells obtained by the culture medium and method of the present invention can further differentiate into mature forebrain neurons, which showed the expression of both BF1 and βIII tubulin (FIG. 12). Moreover, FIG. 13 illustrated that the neuroepithelial cells are susceptible for patterning factors to become regional specific neurons. For instance, after the treatment of 50 ng/ml FGF8b and 200 ng/ml Shh, the neuroepithelial cells in sample 1 and 3 were patterned to became midbrain dopaminergic neurons, featured with the expression of tyrosine hydroxylase.

Figure 14:
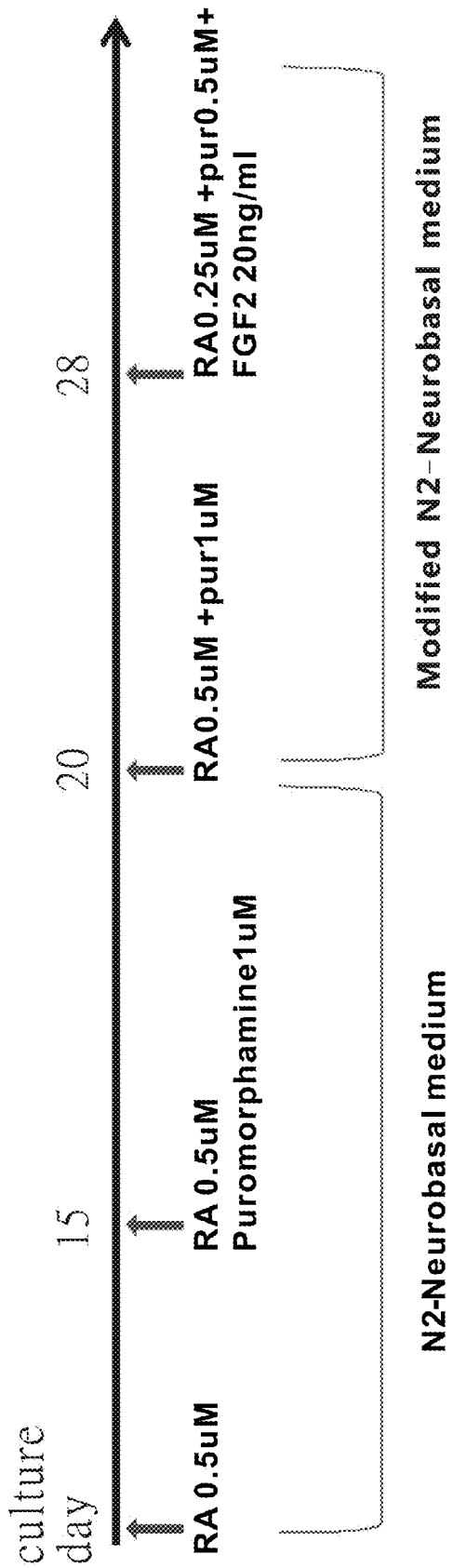
FIG. 14 shows the protocols of culturing the neuroepithelial cells into the motor neurons.
Figure 16:
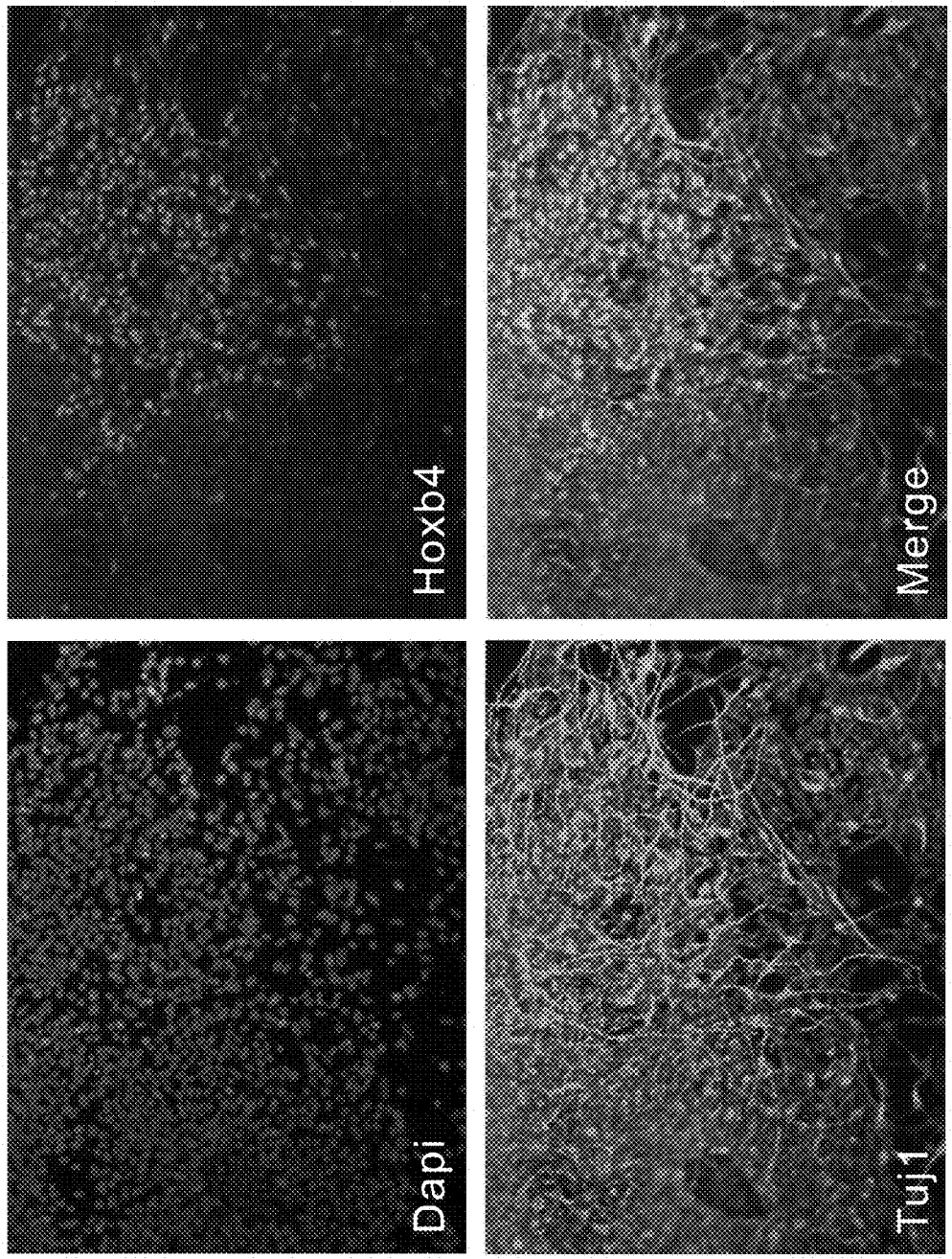
FIG. 16 shows the expression patterns of Hoxb4 and βIII tubulin in the cultured cells with treating retinoic acid and sonic hedgehog at the culture day 15 by immunofluorescence staining.
Figure 17:
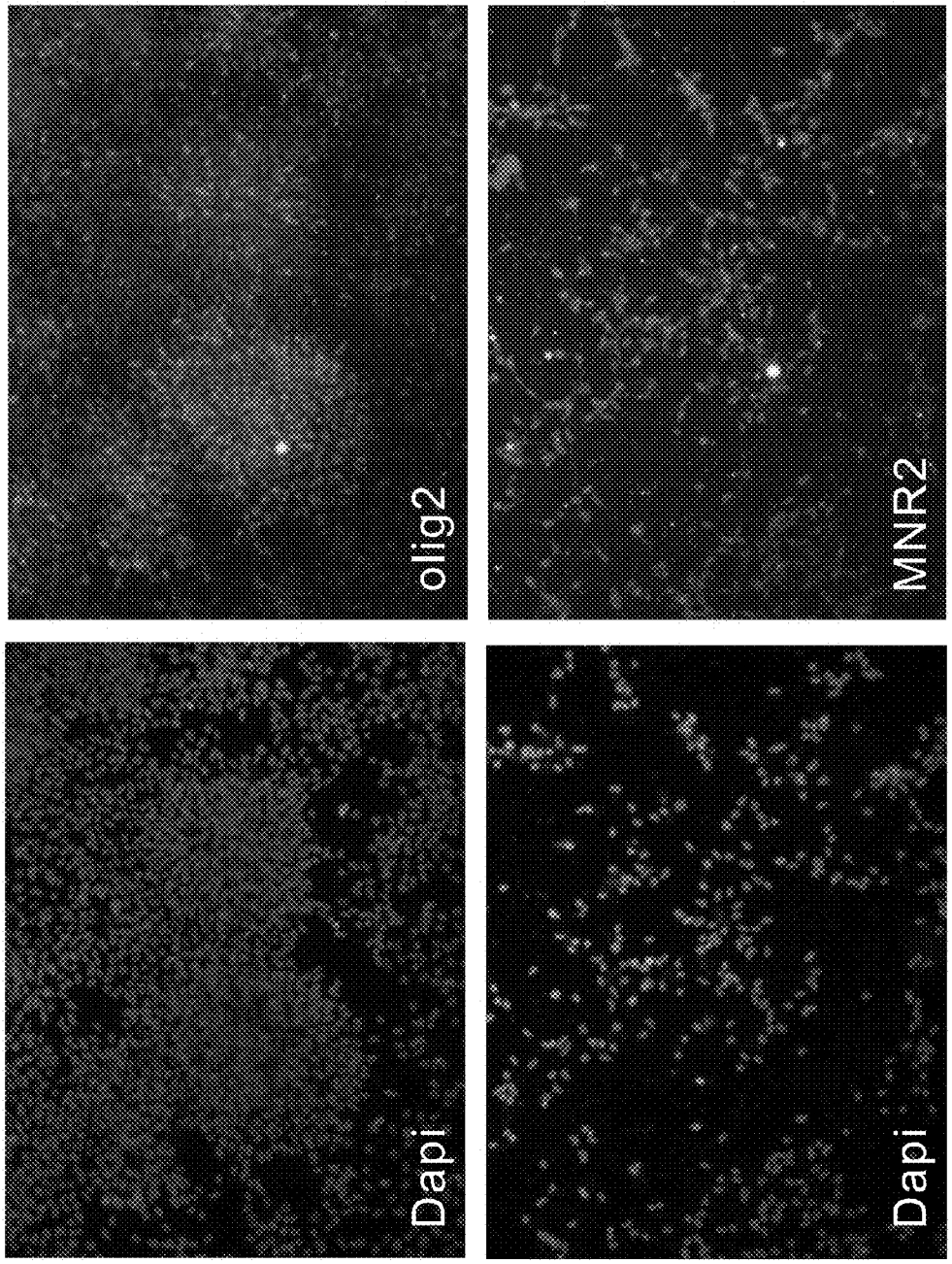
FIG. 17 shows the expression patterns of olig2 and MNR2 in the cultured cells with treating retinoic acid and sonic hedgehog at the culture day 20 by immunofluorescence staining.

To further illustrate the differentiation potency of the ESC-derived neuroepithelial cells, the cells were patterned by 0.1 μM retinoic acid (RA) and 100 ng/ml sonic hedgehog (Shh) to become spinal cord motor neurons. The differentiating protocol is shown in FIG. 14. The cell fate of motor neurons was investigated by immunocytostaining of motor neuronal markers. FIG. 15 shows that treating RA, a caudalizing factor, steered the expression of Hoxb4 in the ESC-derived neuroepithelial cells, a regional marker in the hindbrain and spinal cord. Importantly, treating RA and Shh robustly steered over 70% ESCs converting into spinal cord motor neurons, featured with the expression of the Hoxb4, Oligo2 and MNR2 (FIGS. 16, 17). According to the above results, it showed that the neuroepithelial cells of the invention have the ability to efficiently differentiate into the motor neurons of spinal cord.

The inventors have clearly demonstrated that the method and the medium of the present invention can not only shorten the induction time cost, but also increases the purity of ESC-derived neuroepithelial cells. Following, the neuroepithelial cells could be further induced to become mature neurons for the applications in regeneration medicine and drug discovery against neural disorders.

Without departing from the spirit and scope of the present invention, in view of the present disclosure, anyone skilled in the art may make various changes and modification to the components of medium or the steps of method, which falls the protected scope of the present invention.

Notably, it is understood that the present invention is not limited to the particular embodiments disclosed, but it is intended to cover modifications within the spirit and scope of the present invention as defined by the claims.

We claim:

1. A method for inducing differentiation of pluripotent stem cells into neuroepithelial cells, comprising steps of:
   a. culturing pluripotent stem cells into differentiating cells, wherein the pluripotent stem cells are selected from a group consisting of human embryonic stem cells (hESCs) and induced pluripotent stem cells (iPSCs); and
   b. culturing the differentiating cells in a culture medium under a suitable condition for two days to produce the neuroepithelial cells, wherein the culture medium comprising BIO as a Wnt signal agonist at a concentration of 0.5 μM, SB431542 as a Smad2/3 inhibitor at a concentration of 10 μM and FGF2 as a growth factor and the culture medium is a feeder free culture, and wherein at least 70% of the pluripotent stem cells differentiate into neuroepithelial cells.

2. The method according to claim 1, wherein a bone morphogenetic portion (BMP) signaling inhibitor is absent from the culture medium.

3. The method according to claim 2, wherein the BMP signaling inhibitor is selected from the group consisting of noggin and dorsomorphin (compound C).

4. The method according to claim 1, wherein the concentration of the FGF2 ranges from 1 ng/ml to 100 ng/ml.

* * * * *